United States Patent [19]

Walder-Utz et al.

[11] Patent Number: 5,779,720
[45] Date of Patent: Jul. 14, 1998

[54] ONE-PIECE SURGICAL CLIP

[75] Inventors: Alice Walder-Utz, Zurich; Werner Fritz Dubach, Maur, both of Switzerland

[73] Assignee: Createchnic AG, Dietlikon, Switzerland

[21] Appl. No.: 687,577

[22] PCT Filed: Feb. 2, 1995

[86] PCT No.: PCT/CH95/00023

§ 371 Date: Aug. 9, 1996

§ 102(e) Date: Aug. 9, 1996

[87] PCT Pub. No.: WO95/21575

PCT Pub. Date: Aug. 17, 1995

[30] Foreign Application Priority Data

Feb. 11, 1994 [CH] Switzerland ............... 415/94

[51] Int. Cl.[6] ............................................. A61B 17/08
[52] U.S. Cl. ..................... 606/151; 606/142; 606/143; 606/157
[58] Field of Search ....................... 606/142, 143, 606/151, 157, 144; 227/901, 902

[56] References Cited

U.S. PATENT DOCUMENTS

| | | | |
|---|---|---|---|
| 3,601,127 | 8/1971 | Finegold | 128/337 |
| 4,217,902 | 8/1980 | March | 128/325 |
| 4,556,058 | 12/1985 | Green | 128/305 |
| 4,586,503 | 5/1986 | Kirsch et al. | 128/334 R |
| 4,589,626 | 5/1986 | Kurtz et al. | 251/10 |
| 4,791,707 | 12/1988 | Tucker | 227/19 |
| 4,796,627 | 1/1989 | Tucker | 128/337 |
| 5,026,379 | 6/1991 | Yoon | 606/141 |

Primary Examiner—Michael Buiz
Assistant Examiner—Tina T. D. Pham
Attorney, Agent, or Firm—Weingarten, Schurgin, Gagnebin & Hayes LLP

[57] ABSTRACT

The surgical clip (1) with an approximate C-shaped cross-section has two lateral jaws (10) interconnected by a web (12). The two jaws (10) end in pressure edges (11) which thus define a clamping gap (15). There is a centric recess (13) perpendicular to the direction of the two pressure edges (1) roughly in the middle, passing through the web (12) on the one hand and partly through the two jaws (10) below it. This design makes it possible to stack the surgical clips of the invention and secure them on a storage unit. This makes it possible for the first time to apply surgical clips in rapid sequence by means of a simple fitting device. There are inwardly directed retaining ribs (17) on the inner surfaces (16) of the jaws (10) to position the clips on the storage unit.

8 Claims, 2 Drawing Sheets

ONE-PIECE SURGICAL CLIP

FIELD OF THE INVENTION

The present invention is related to surgical clips, and more particularly to surgical clip delivery systems.

BACKGROUND OF THE INVENTION

After every surgical operation, the healing of the wound is of major importance. Attempts have therefore been made to create optimal conditions for the most risk-free, pain-free and fastest healing. It is known that wounds whose edges are held together by clips or thread heal faster and cosmetically better than wounds that are left alone to heal (Williams and Harrison 1977). When surgical clips are used, the infection rate is lower, granulomas do not occur and the average length of the patient's hospital stay is shorter than when thread is used (Beresford et al, 1984). Clips are preferred for skin burns, because they are much faster to apply than a suture. A skin transplant can be attached more quickly, and critical anesthesia time can therefore be reduced (Kahn et al. 1984, Hallock et al. 1984).

Due to the reduced traumatization of the tissue compared to a suture, clamping produces better results in healing wounds and less scar formation. According to Neckemann (1965/1968), sutures leave scars at the puncture points and at the places where the thread is tied or presses on the tissue for some time. Surgeons therefore try to keep the number of puncture points and their size as small as possible to prevent the known "rope ladder" syndrome as much as possible.

Not only are surgical clips simple and fast to attach and remove, but the risk of germs growing on the surgical clips is low. In contrast, using sewing materials in the wound increases the risk of virulence from staphylococci some 10,000 times. The abscess rate is roughly three times lower with clip technology. According to Stephens (1990), wounds closed with clips exhibit better mechanical properties on the seventh day post-op than those closed with surgical thread. This means that the modulus of elasticity is greater, the tensile strength higher and the capacity for wound absorption without rupture is better. Lowdon et al. (1992) also found that post-operative complications in the form of anastomotic weaknesses, wound infection and bleeding are around 25% rarer when clips are used.

Conventional clips for attachment to parts of the body penetrate both sides of the skin on the wound to be held together in several places. For one thing, this penetration is painful to the patient and, for another, it is unfavorable for medical reasons. Besides the cosmetic effect due to the puncture, it also increases the risk of infection, since foreign material can get into the wound. And in many clip systems, a special instrument is required to remove the clips.

Most of the disadvantages associated with the use of thread have also occurred with the newer systems with staples. In spite of this, closing a wound with staple systems has become very widespread. In contrast to making a suture, the staple method requires less routine and is extremely fast due to the staplers in which the staples are stored. On the other hand, a special instrument is required to remove the staples.

Various surgical clips with relatively simple designs are known from the patent literature. Thus, U.S. Pat. No. 3,601,127 shows a surgical clip that consists of two semicircular clamping jaws that are connected to one another by a spring-mounted central web. The pressure edges of the jaws are toothed and perforate the edges of the wound.

On the other hand, EP-A-224,500 shows a surgical clip that consists of two movable jaws each with a grip, and pressure edges that are wavy, so there is no perforation of the edges of the wound.

From FR-A-419,096, one-piece spring-mounted, curved surgical clips with two pressure edges facing one another are known, where two jaws connected to one another by a web form the pressure edges. The simplicity of these surgical clips is attractive, but they require a special forceps to be used. Each clip must also be inserted individually into the forceps before it can be used.

WO-88/01487 shows surgical clips, which are held by means of pressure edges on a storage element that goes through the surgical clip through a hole in the web. A slit extending from the hole to a pressure edge serves as a feed to a spreader.

SUMMARY OF THE INVENTION

The task of this invention is therefore to create a one-piece, spring-mounted, curved surgical clip with two pressure edges facing one another that is made of two jaws connected to one another by a web, so that it is suitable for use in many instruments used to insert surgical clips.

This task is solved in the most general form by giving the surgical clip means of holding it in a stack.

In one preferred form of embodiment, the means of holding them in a stack consists of a longitudinal, central cut, which is made through the web and the two jaws perpendicular to the pressure edges. Surgical clips made in this way can then be stacked on a specially designed holder like a skewer.

One alternative is that the means for the stackable holder, on at least one of the two lateral front surfaces of the surgical clip, is a recess that goes through both the web and the two jaws via the pressure edges. In this case, the surgical clips are stacked and guided by storage elements on one or both sides.

So that the surgical clips so stored by means of a storage element can also still be attached, it is advantageous if there are means on the inside of the jaws for holding the surgical clips in a spread-out position. This can be done very easily by designing these means as retaining ribs running some distance away from the pressure edges.

Other advantageous forms of embodiment will emerge from the other dependent patent claims and are explained in the description below.

BRIEF DESCRIPTION OF THE DRAWINGS

The enclosed drawings show various forms of embodiment of the object of the invention which are explained in the description below, wherein.

DESCRIPTION OF THE INVENTION

Figure 1:
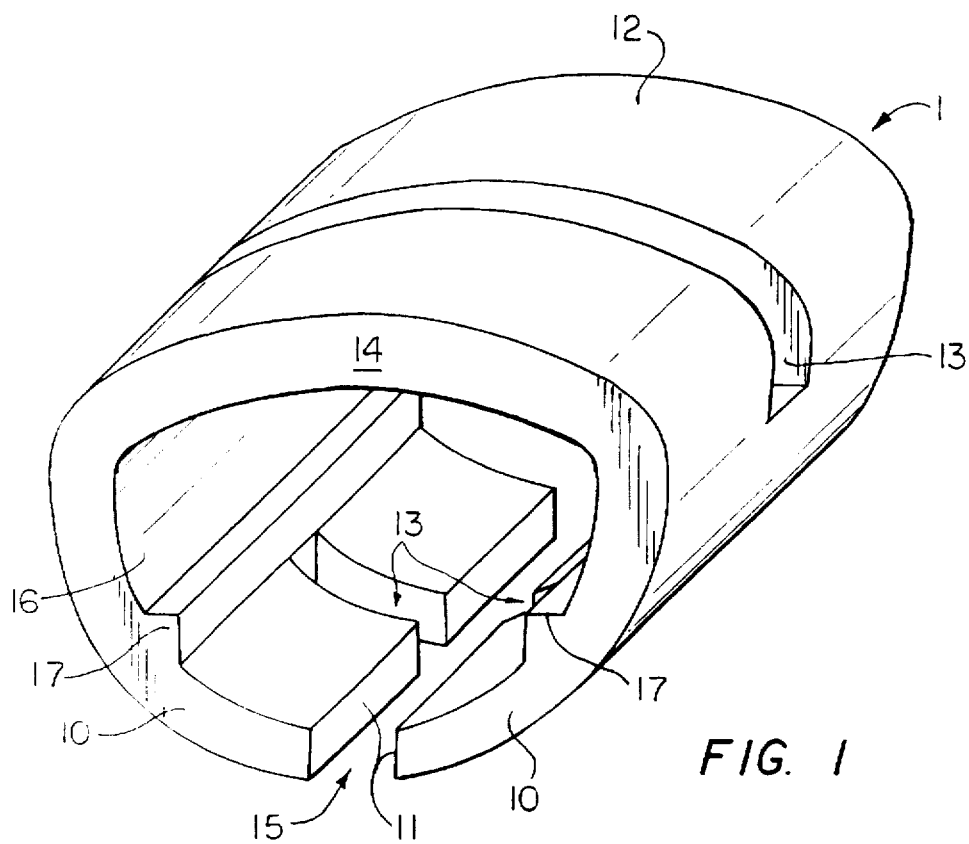
FIG. 1 shows a perspective view of one preferred form of embodiment of the surgical clip in the invention.
Figure 2:
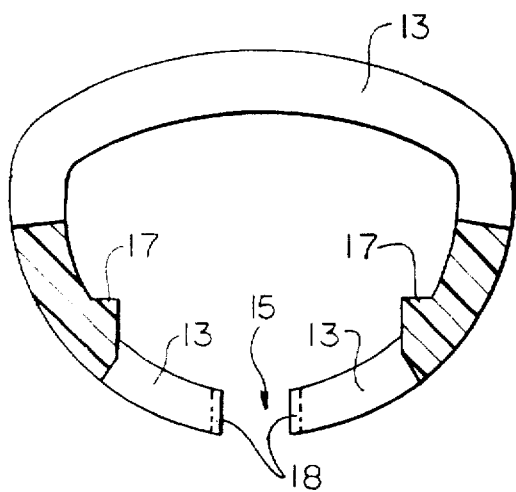
FIG. 2 shows a cross section through the middle of the same surgical clip perpendicular to the pressure edges.
Figure 3:
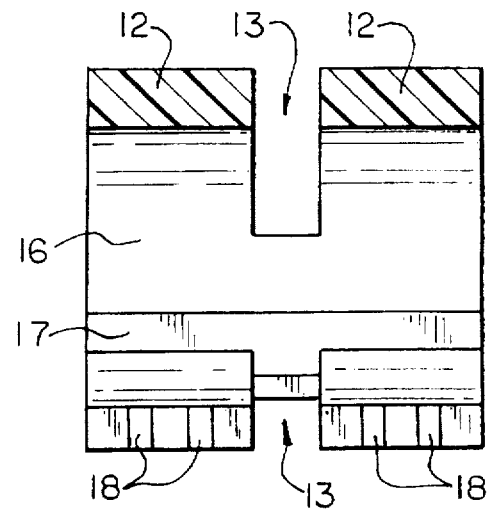
FIG. 3 shows a central longitudinal section parallel to the pressure edges.

The preferred form of embodiment of the surgical clip in the invention, as shown in FIGS. 1–4, is made out of plastic. The drawing in FIGS. 1–3 shows the surgical clip enlarged approximately 10–15 times. In principle, this design can also be made of surgical steel. But the surgical clip is preferably made out of a transparent plastic, to guarantee visual control of the suture during the healing process. The surgical clip basically consists of two clamping jaws 10, which are connected to one another in one piece by a common web 12. The ends of the jaws 10 form the pressure edges 11, which together form a gap 15. The two jaws 10 and the web 12 together form a hollow cylindrical element with a roughly oval cross section. The two pressure edges 11 run parallel to the longitudinal axis of this hollow cylindrical element. Perpendicular to the longitudinal axis of the hollow cylindrical element is a central cut 13, which goes through the web 12 completely and the two jaws 10 partially. In the area of the jaws 10, the central cut extends out over the gap 15 and thus divides the two pressure edges 11. While the form of the cross section of the surgical clip is thus roughly C-shaped on both sides of the central cut, in the area of the central cut 13, on both sides there remains only a solid connecting bridge of the respective jaw 10. This can be seen most clearly in FIG. 2. Since the pressure edges 11 are divided by the central cut 13, the pressure edges 11 may also run in a straight line. But to guarantee an especially good blood flow in the clamping area as well, the pressure edges 11 are advantageously provided with wavy depressions 18, as shown in FIGS. 2 and 3. The design of the pressure edges 11 can however be varied, as desired.

In turn, parallel to the longitudinal axis of the surgical clip, parallel to the pressure edges 11 and perpendicular to the direction in which the central cut 13 runs, on the inside 16 of the jaws 10, there is a retaining rib 17. The central cut 13 in the area of the jaws 10 extends only up to the retaining ribs 17, but does not go through them. The significance and function of the retaining ribs 17 will be discussed later on.

Figure 6:
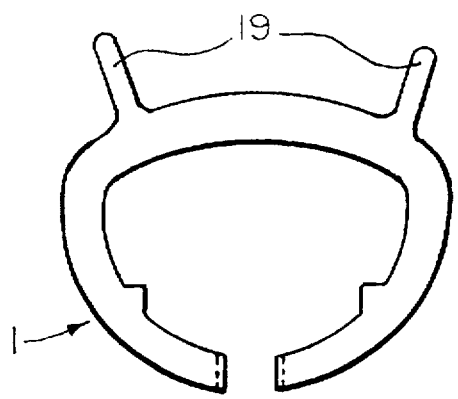
FIG. 6 shows a surgical clip according to the design in FIGS. 1–4 which also has spreading elements.
Figure 4:
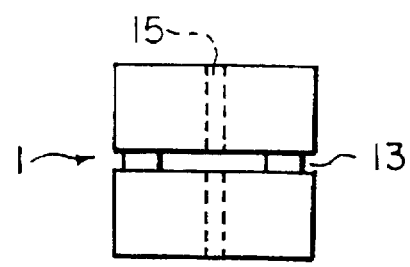
FIG. 4 shows a top view of the surgical clip in FIGS. 1–3 on a smaller scale.
Figure 5:
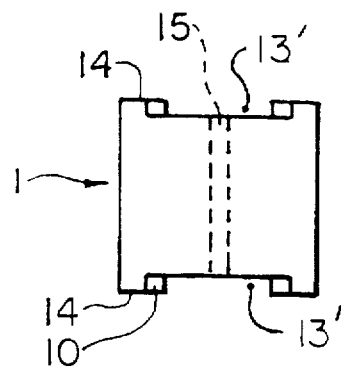
FIG. 5 shows another form of embodiment of the surgical clip with two lateral recesses for the stackable holder.

While the means of stacking and holding the surgical clip 1 have thus far consisted of a central cut 13 in the embodiment described, FIG. 5 shows a variation in which the clip does not have anything going through the middle of it, but instead has a corresponding lateral recess 13', which can perform the same function. In the embodiment in FIG. 5, the lateral recesses 13' are made in both lateral front surfaces 14 of the surgical clip. But depending on the design of the storage element, a single lateral recess 13' may suffice. For positioned storage of the surgical clips 1 in the variation in FIG. 5, they were inserted on a rail that is rectangular in cross section or U-shaped and has a storage element on one or both sides. The storage element would hold the surgical clips positioned and stacked and by means of same allow the surgical clips to be transported in stages. The lateral recesses 13' extend largely beyond the web 12 and also go through the clamping jaws 10 lying beneath. As in the variation described above, where the central cut 13 in the web 12 is longer than the sum of the two cuts in the two jaws 10, the length of the recess 13' in the web 12 is also longer than the sum of the two lateral recesses from both the jaws 10 found below. Both variations of the surgical clips in FIGS. 4 and 5 can also be provided with spreading elements 19, as the surgical clip 1 in FIG. 6 shows. The spreading elements 19 consist of two little walls projecting radially from the surface of the web 12. They are arranged on the web 12 near the neck area of the jaws 10. The surgical clips can be held on the spreading elements 19, where pressure can be exerted against one another, which causes the surgical clip to spread out. This does not exert enough force on the surgical clips to spread the jaws wide enough to set the surgical clip, but the spread that can be achieved is sufficient to remove the surgical clip from the healed suture without any special aids. The arrangement of the spreading elements 19 does not prevent them from being able to be stacked. If the surgical clip has a central cut 13, this cut also extends through the two spreading elements. But if the surgical clip is made like the variation in FIG. 5, then the two spreading elements 19 extend crosswise over the web 12 from one lateral recess to another.

The special design of the surgical clip in the invention now makes it possible not only to stack the clips, but also to position them on a storage element 20 adapted to them in a predetermined position. This is shown clearly in FIG. 7. The storage element 20 consists, for example, of a sword punched out of surgical steel, on which the surgical clips are held stacked one over the other. The two lateral cuts in the sword are designed like sawteeth. The distance between two positioning notches Z1 on the same cutting side corresponds to the height of the surgical clip. The narrowest width of the storage element 20, that is the distance between two positioning notches 21 opposite one another, thus corresponds exactly to the length of the central cut 13 in the jaws 10. Consequently, all surgical clips except for the lowest surgical clip on the storage element 20 are held completely released in the position shown. On the lowest end, the storage element is expanded so that the surgical clip held is completely spread. The front end of the storage element 20 opens into a two-pronged spreader fork 22, which leaves a free space 23 between the two prongs. Now, the storage element 20 forms part of a surgical clip fastening instrument, so it can be set on the skin over the two edges of the wound, wherein the two turned-up edges of the wound have room in the free space 23. Now, if the surgical clips are held back by means not shown, while the sword-shaped storage element is pulled up a step, the lowest surgical clip, which is spread, will be pushed off the storage element and at the same time will hold the two opposite edges of the wound together with its two pressure edges 11. At the same time, all surgical clips above it will be moved down a notch. Thus, only the surgical clips in the invention can be easily pushed, spread and set on the wound by the back and forth movement of the storage element 20. The condition for this working, however, is the ability of the surgical clips to be stacked and positioned precisely. This can be done in an extremely simple way with the invention.

The principle of storing the surgical clips which have lateral recesses 13' as a means of holding them works in an almost the same way. In the embodiment in FIG. 5, the storage element can consist of two parallel sword-shaped parts, which are almost identical to the one in FIG. 7. For precise guidance, the two storage elements can be connected to one another.

Figure 7:
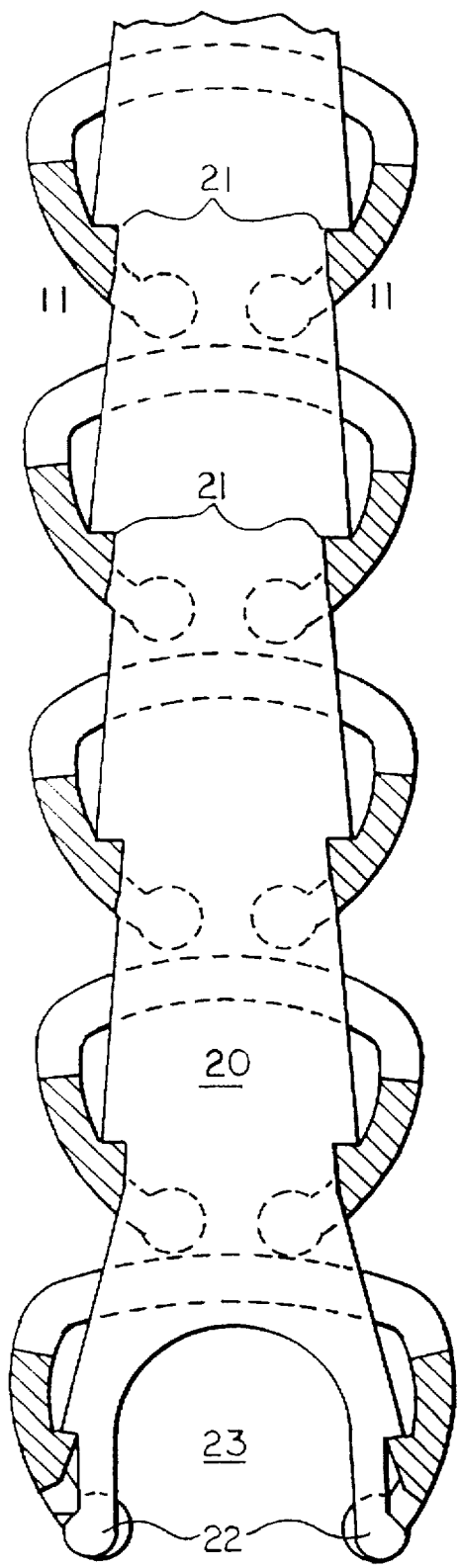
FIG. 7 shows several surgical clips lined up in a stacked arrangement on a storage element.

The surgical clips in FIG. 7 show that the pressure edges 11 do not have to be simply flat. They are shown thickened like a bulge. Although the different corners and edges are shown with sharp edges in the figures, preferably those edges and corners that come in contact with the patient's skin will be partially rounded.

It should be understood that various modifications to the above described invention may be made without departing from the inventive concepts disclosed herein. Accordingly, the present invention is not to be viewed as limited to the described embodiments.

What is claimed is:

1. A one-piece, spring-mounted, curved surgical clip and a storage element as a retaining device, comprising:

first and second pressure edges which face one another, and which are formed by two jaws connected to one another via a web and means for stackably holding on a storage element that goes through them, characterized by the fact that the holding means have at least one cut or one recess, which crosses the web and the pressure edges of the jaws perpendicular to the direction in which the pressure edges run and by the fact that the jaws have retaining ribs running parallel to and some distance away from the pressure edges, said clip being stackably held on a storage element disposed therethrough, said storage element having a sword-like form with lateral cuts forming positioning notches, wherein the distance between adjacent positioning notches corresponds to the height of the surgical clip, said retaining ribs being in contact with said positioning notches upon stacking.

2. The surgical clip according to claim 1, further including, central cut running perpendicular to the pressure edges, which goes through the web completely and through the two jaws thereunder near the pressure edges.

3. The surgical clip according to claim 1, further including a recess made in at least one of the two lateral fronts of the surgical clip, said recess bordering the at least one recess which crosses the web and the pressure edges of the jaws perpendicular to the direction in which the pressure edges run.

4. The surgical clip according to claim 1, wherein the pressure edges are wavy.

5. The surgical clip according to claim 1, further including two upward-projecting spreader elements arranged on the web and outside the area of the retaining ribs.

6. The surgical clip according to claim 2, wherein the length of the central cut in the web is longer than the length of the cut in the two jaws together.

7. The surgical clip according to claim 3, wherein the length of the recess in at least one of the lateral front surfaces, in the web is longer than the length of the recess in the two jaws together.

8. The surgical clip according to claim 1, wherein said clip is made of a transparent plastic.

* * * * *